US 10,647,630 B2

(12) United States Patent
Stochniol et al.

(10) Patent No.: US 10,647,630 B2
(45) Date of Patent: *May 12, 2020

(54) COMBINED PREPARATION OF AT LEAST BUTENE AND OCTENE FROM ETHENE

(71) Applicant: Evonik Operations GmbH, Essen (DE)

(72) Inventors: Guido Stochniol, Haltern am See (DE); Stephan Peitz, Oer-Erkenschwick (DE); Dietrich Maschmeyer, Recklinghausen (DE); Helene Reeker, Dortmund (DE); Joerg Schallenberg, Dorsten (DE)

(73) Assignee: Evonik Operations GmbH, Essen (DE)

(*) Notice: Subject to any disclaimer, the term of this patent is extended or adjusted under 35 U.S.C. 154(b) by 127 days.

This patent is subject to a terminal disclaimer.

(21) Appl. No.: 15/000,837

(22) Filed: Jan. 19, 2016

(65) Prior Publication Data
US 2016/0207849 A1 Jul. 21, 2016

(30) Foreign Application Priority Data

Jan. 19, 2015 (EP) .................... 15151624

(51) Int. Cl.
C07C 2/24 (2006.01)
C07C 7/04 (2006.01)
C07C 2/10 (2006.01)

(52) U.S. Cl.
CPC ............. C07C 2/24 (2013.01); C07C 2/10 (2013.01); C07C 7/04 (2013.01); C07C 2521/12 (2013.01); C07C 2523/755 (2013.01)

(58) Field of Classification Search
None
See application file for complete search history.

(56) References Cited

U.S. PATENT DOCUMENTS 2,581,228 A 1/1952 Bailey et al.
2002/0045790 A1* 4/2002 Stibrany .................. C07C 2/32
585/521

(Continued)

FOREIGN PATENT DOCUMENTS

CN 103172485 A 6/2013
JP 2003-326169 A 11/2003
WO WO 2014/154798 A1 10/2014

OTHER PUBLICATIONS

Ye et al. "A Tandem Catalytic System for the Synthesis of Ethylene-Hex-1-ene Copolymers from Ethylene Stock", Macromolecular Rapid Communications, 2004, 25, 647-652.*

(Continued)

Primary Examiner — Ali Z Fadhel
(74) Attorney, Agent, or Firm — Grüneberg and Myers PLLC

(57) ABSTRACT

A process for the combined preparation of at least butene and octene from ethane, proceeds by a) providing an inert solvent having a boiling point or boiling range below the boiling point of butene; b) providing a first feed mixture comprising at least the inert solvent and ethene dissolved therein; c) converting the first feed mixture in a first synthesis; d) in the first synthesis, oligomerizing at least a portion of the ethene present in the first feed mixture in the presence of a first heterogeneous catalyst and in the presence of the inert solvent to obtain a first reaction mixture comprising at least the inert solvent, butene, hexene and octene; e) working-up of the first reaction mixture and/or a substance stream based thereon into a low boiler fraction comprising the inert solvent, at least one $C_4$-fraction comprising butenes, a $C_6$-fraction comprising hexenes, a $C_8$-fraction comprising octenes and into a $C_{8+}$-fraction comprising hydrocarbons having more than eight carbon atoms; f) using at least a portion of the low boiler fraction for (Continued)

providing the first feed mixture; g) providing a second feed mixture comprising at least hexene and ethene dissolved in the hexene using at least a portion of the $C_6$-fraction; h) converting the second feed mixture in a second synthesis, wherein the second synthesis is spatially separated from the first synthesis; i) in the second synthesis, reacting at least a portion of the ethene present in the second feed mixture with at least a portion of the hexene present in the second feed mixture in the presence of a second heterogeneous catalyst to obtain a second reaction mixture comprising at least octene; and k) joint working-up of the second reaction mixture with the first reaction mixture or with the substance stream based thereon.

17 Claims, 4 Drawing Sheets

(56) References Cited

U.S. PATENT DOCUMENTS

| | | | |
|---|---|---|---|
| 2006/0135832 A1* | 6/2006 | Vora | B01D 3/14 |
| | | | 585/517 |
| 2007/0185360 A1* | 8/2007 | Buchanan | C07C 2/32 |
| | | | 585/521 |
| 2007/0185362 A1* | 8/2007 | Lattner | C07C 2/32 |
| | | | 585/521 |
| 2007/0191661 A1* | 8/2007 | Brown | C07C 2/12 |
| | | | 585/517 |
| 2009/0312583 A1* | 12/2009 | Sigl | C07C 2/12 |
| | | | 568/909 |
| 2010/0268006 A1* | 10/2010 | Gildenhuys | C07C 2/36 |
| | | | 585/313 |
| 2011/0124938 A1* | 5/2011 | Inoue | B01J 23/755 |
| | | | 585/533 |
| 2011/0288256 A1 | 11/2011 | Vermeiren | |
| 2011/0301398 A1* | 12/2011 | Heidemann | C07C 2/10 |
| | | | 585/512 |
| 2012/0016097 A1* | 1/2012 | Weber | C07C 2/30 |
| | | | 526/348 |
| 2013/0158321 A1 | 6/2013 | Olivier-Bourbigou et al. | |
| 2014/0012059 A1* | 1/2014 | Vinel | C07C 7/04 |
| | | | 585/809 |
| 2015/0126790 A1* | 5/2015 | Venter | C07C 2/36 |
| | | | 585/511 |
| 2016/0194572 A1* | 7/2016 | Lilga | C10G 29/205 |
| | | | 585/14 |

OTHER PUBLICATIONS

Fadhel et al. "Combining the Benefits of Homogeneous and Heterogeneous Catalysis with Tunable Solvents and Nearcritical Water", Molecules 2010, 15, 8400-8424.*

Written Opinion dated May 20, 2016 in Singaporean Patent Application No. 10201600311W filed Jan. 15, 2016.

Combined Office Action and Search Report dated Dec. 29, 2016 in Taiwanese Patent Application No. 105101070 (submitting English translation only).

Combined Office Action and Search Report dated Sep. 11, 2017 in Chinese Patent Application No. 201610152365.5 (with English translation of categories of cited documents).

* cited by examiner

COMBINED PREPARATION OF AT LEAST BUTENE AND OCTENE FROM ETHENE

BACKGROUND OF THE INVENTION

Field of the Invention

The invention is concerned with the combined preparation of at least butene and octene from ethene.

Discussion of the Background

Hydrocarbons are chemical compounds which consist exclusively of carbon C and hydrogen H. Alkenes (synonym: olefins) are hydrocarbons which have a C=C double bond in the molecule. Alkanes (synonym: paraffins), on the other hand, are hydrocarbons which have only single bonds. They are therefore also referred to as saturated.

In organic chemistry, hydrocarbons are frequently designated according to the number of carbon atoms which they have per molecule, by the respective class of substances being preceded by the prefix $C_n$. Here, n is the respective number of carbon atoms in a molecule. Thus, $C_4$-olefins are substances from the class of alkenes having four carbon atoms. $C_8$-olefins correspondingly have eight carbon atoms per molecule. Where the prefix $C_{n+}$ is used in the following, it refers to a class of substances which have more than n carbon atoms per molecule. A $C_{4+}$-olefin accordingly has at least five carbon atoms.

The simplest olefin is ethene (ethylene). It has two carbon atoms. Ethene is an important basic chemical and is therefore prepared in large quantities. This is usually effected by steam cracking of naphtha. In addition, it can be obtained by dehydrogenation of ethane, which in turn is a constituent of natural gas. Owing to the increasing exploitation of unconventional sources of natural gas and decreasing recovery of petroleum, the proportion of ethene based on natural gas is steadily increasing.

$C_4$-olefins encompass the four isomeric materials 1-butene, cis-2-butene, trans-2-butene and isobutene. 1-Butene and the two 2-butenes belong to the group of the linear butenes, while isobutene is a branched olefin. The linear $C_4$-olefins 1-butene, cis-2-butene and trans-2-butene are often summarized as "n-butene" in the literature. Depending on the thermodynamic circumstances, the four isomeric $C_4$-olefins usually occur together. For this reason, no distinction between singular and plural is made when the term "butene" is used. When reference is made here to "butene" with no further details being specified, what is meant is a linear alkene having four carbon atoms (or n-butene) or a mixture containing different isomeric alkenes having four carbon atoms.

A current overview of the chemical and physical properties of butenes and also the industrial processing and utilization thereof is given by:

F. Geilen, G. Stochniol, S. Peitz and E. Schulte-Koerne: Butenes. Ullmann's Encyclopedia of Industrial Chemistry. (2013)

Butenes are nowadays predominantly obtained in the cracking of petroleum fractions in a steam cracker or in a fluid catalytic cracker (FCC) and are used as intermediate for the preparation of a variety of industrial chemicals.

In the following, a "hexene" is an olefin having six carbon atoms or a mixture containing a plurality of different $C_6$-olefins. For this reason, no distinction is made between singular and plural when using the term "hexene". The $C_6$-olefins include the eighteen isomers 1-hexene, (E)-2-hexene, (Z)-2-hexene, (E)-3-hexene, (Z)-3-hexene, 2-methyl-1-pentene, 2-methyl-2-pentene, (R)-3-methyl-1-pentene, (S)-3-methyl-1-pentene, (E)-3-methyl-2-pentene, (Z)-3-methyl-2-pentene, 4-methyl-1-pentene, (E)-4-methyl-2-pentene, (Z)-4-methyl-2-pentene, (3S)-2,3-dimethyl-1-butene, (3R)-2,3-dimethyl-1-butene, 2,3-dimethyl-2-butene and 3,3-dimethyl-1-butene.

However, only the substances 1-hexene and 4-methyl-1-pentene, which are used as monomers or comonomers in the production of plastics, are of industrial interest. For this purpose, they are prepared from ethene or from the $C_3$-olefin propene by oligomerization. The oligomerization will be explained in detail below.

For the purposes of the present invention, octene is an olefin having eight carbon atoms or a mixture containing a plurality of different $C_8$-olefins. The $C_8$-olefins include a large number of isomers which are too many to list here. An industrially important representative of the $C_8$-olefins is 1-octene which is prepared by oligomerization of ethene and is used as comonomer in polyethylene.

An alternative way of preparing octene is dimerization of n-butene. The mixture of olefins having eight carbon atoms which is formed here is referred to as dibutene, and is thus a particular octene within the meaning of the terminology employed here. Dibutene is distinguished by the isomer distribution, in terms of which it differs from other octene mixtures.

Depending on the way in which the individual n-butene molecules are joined in the course of the oligomerization, an oligomer having a different degree of branching is obtained. The degree of branching is described by the iso index, which states the mean number of methyl groups per $C_8$ molecule in the isomer mixture. The iso index for dibutene is defined as follows:

$$\text{Iso index} = (\text{proportion by weight of methylheptenes} + 2 * \text{proportion by weight of dimethylhexenes})/100$$

Thus, n-octenes contribute 0, methylheptenes contribute 1 and dimethylhexenes contribute 2 to the iso index of a product mixture of $C_8$-olefins. The lower the iso index, the less branched are the molecules in the mixture. The opposite of branched in this context is linear. A product with high linearity accordingly has a low degree of branching.

A low degree of branching is always important when the olefin mixture is to be used as starting material for preparing plasticizers. Scientific studies demonstrate that the degree of branching of olefin mixtures which are processed further by hydroformylation, hydrogenation and esterification to give plasticizers is critical to the properties and quality of the plasticizer.

The iso index which a $C_8$-olefin mixture has to achieve in order to be able to serve as starting material for high-quality plasticizers depends on the respective requirements of the plasticizer customers and changes over time. At present, an iso index of less than 1.1 is usually required.

For the purposes of the present invention the oligomerization which has now been mentioned a number of times is the reaction of hydrocarbons with themselves, forming corresponding longer-chain hydrocarbons. Olefins having from two to eight carbon atoms can be oligomerized very readily.

Thus, for example, an olefin having six carbon atoms (hexene) can be formed by oligomerization of two olefins having three carbon atoms. The oligomerization of two molecules with one another is also referred to as dimerization. If, in contrast, three olefins having three carbon atoms are joined to one another (trimerization), the result is an olefin having nine carbon atoms. If n-butene is subjected to an oligomerization, essentially olefins having eight carbon atoms (more precisely: dibutene) and also olefins having twelve carbon atoms (C$_{12}$-olefins, "tributene") and to a lesser extent olefins having more than twelve carbon atoms (C$_{12}$+-olefins, called "tetrabutene") are formed.

One process employed in industry for preparing dibutene by oligomerization of n-butene is the OCTOL® process. Detailed description thereof can be found in the nonpatent literature, for example in:

B. Scholz: The HÜLS OCTOL Process: Heterogeneously catalyzed dimerization of n-butenes and other olefins. DGMK conference in Karlsruhe, published in Erdöl, Erdgas, Kohle, April 1989, pages 21 and 22.

R. H. Friedlander, D. J. Ward, F. Obenaus, F. Nierlich, J. Neumeister: Make plasticizer olefins via n-butene dimerization. Hydrocarbon Processing, February 1986, pages 31 to 33.

F. Nierlich: Oligomerize for better gasoline. Hydrocarbon Processing, February 1992, pages 45 to 46.

In the patent literature, an oligomerization based on the OCTOL® process is described, for example, in DE102008007081A1. EP1029839A1 is concerned with the fractionation of the C$_8$-olefins formed in the OCTOL® process.

The completely heterogeneously catalyzed OCTOL® process gives a dibutene which has a low degree of branching and is highly suitable for the preparation of plasticizers. Heterogeneously catalyzed means that the catalyst is present as a solid in the liquid or gaseous reaction mixture. The fluid reactants thus flow around the catalyst and the catalyst remains in the reactor. Since the OCTOL® process has been optimized on the processing of C$_4$-olefins as feedstock, it is dependent on the availability of butenes as feedstock. Other raw material sources cannot be processed without extra expense. Since C$_6$-olefins are not obtainable by oligomerization of C4-olefins, the preparation of hexene with the OCTOL® process is not possible. Dibutene, tributene and tetrabutene are exclusively formed. The OCTOL® process is inflexible in this respect.

A greater flexibility with respect to the target product can be achieved by cooligomerization. The term cooligomerization refers to the simultaneous oligomerization of a plurality of substrates in one reaction vessel. Thus, EP2582648B1 describes the cooligomerization of butene and octene to give dodecene (C$_{12}$-olefin). As in the case of any oligomerization, which olefin reacts with which is not precisely known in a cooligomerization: In the example of EP2582648B1, a dodecene can be formed both from three butenes and also from a butene and an octene. From a chemical point of view, any oligomerization can be considered to be a cooligomerization. From an industrial point of view, on the other hand, a cooligomerization is present only when at least two olefins having different numbers of carbon atoms are introduced into a common reactor. In the choice of terminology, it is thus the controllable introduction of the starter materials which matters, not the reaction which actually takes place. The process described in EP2582648B1 is even more flexible with respect to its C8 and C12 target products than an oligomerization which uses exclusively C4 as starter material. Nevertheless, the preparation of hexene is likewise not possible. This is only possible by oligomerization of ethene and/or propene.

WO2005/123884 discloses the combined preparation of 1-octene and 1-hexene by tetramerization and trimerization of ethylene. For this purpose, two different homogeneous catalysts, namely a first catalyst for tetramerization and a second catalyst for trimerization, are provided in a common reaction vessel. Since the homogeneous catalysts used are dissolved in the reaction mixture, they must either be removed therefrom or remain therein. The latter case is then no problem if the reaction mixture is used as comonomer in a polyethylene synthesis. In the preparation of polyethylene, exclusively homogeneous catalysts are in fact used which remain in the polymer and are therefore lost. If however the 1-hexene and 1-octene prepared were required to be specially separated and as far as possible obtained as pure substances, the dissolved homogeneous catalysts had to be first laboriously removed. The process is therefore hardly suitable for the isolated preparation of 1-octene and 1-hexene and makes sense industrially only in connection with polyethylene synthesis.

Furthermore, this process also does not appear to be suitable for preparing C$_8$-olefins for use as starting material for plasticizers: Although up to 52% by weight of C$_8$-olefins are obtained in combined tetramerization and trimerization, the degree of branching is not specified precisely. Moreover, the process is optimized for the production of the comonomer 1-octene, viz. a C$_8$-olefin which in any case is not very suitable for plasticizer production. It is therefore not possible to see that the C$_8$-alkenes achieve an iso index which qualifies them as starting material for plasticizer production. In addition, the homogeneously dissolved catalyst would definitely have to be separated off in this use since the subsequent hydroformylation is likewise homogeneously catalyzed and is sensitive to interference caused by extraneous catalysts introduced by entrainment.

What has just been said also applies to the process disclosed in WO2005/123633 for the oligomerization of ethylene, which is carried out in the presence of cyclohexane. The cyclohexane serves as solvent and is intended to reduce the deactivation of the homogeneous catalyst used or its activator.

A similar situation also applies to US2013/0066128 A1 which is concerned with the homogeneous oligomerization of ethene in n-heptane.

The problem of separating off the catalyst does not arise in heterogeneously catalyzed processes in which the catalyst is present as a solid and remains in the reactor. Ethylene oligomerization over a solid Si/Al/Ni system is described in U.S. Pat. No. 8,637,722B2. However, this process takes place in the gas phase, which is disadvantageous in terms of the utilization of space by the reactors. In addition, the established process steps of further processing of butenes and octenes take place in the liquid phase, so that this gas-phase process is not readily compatible with existing technology. A need to liquefy the butenes and octenes obtained in the gas phase requires additional energy.

The gas-phase process shown in WO2010/117539A1 for the oligomerization of ethylene diluted in a FCC gas over a zeolitic Ni catalyst can also not be incorporated directly into an established production run for C$_4$/C$_8$ utilization.

The same is also true for the heterogeneous gas-phase oligomerization of ethene over a nickel-containing zeolite described in U.S. Pat. No. 4,717,782. The feed mixture can also comprise C$_4$-paraffins and inert gases. U.S. Pat. No. 8,637,722 also describes the oligomerization of ethene in the gas phase over a heterogeneous catalyst of Ni/Al on a support made of Al$_2$O$_3$/SiO$_2$. Inert gases such as nitrogen, argon or helium may be present.

A mixed form between heterogeneous and homogeneous C$_2$-oligomerization is shown in US2013/0158321A1. Here, ethene is firstly dimerized homogeneously to butenes and these are then converted to octenes by heterogeneous catalysis over a solid nickel catalyst. Both reaction stages take place in the liquid phase in the presence of hexane. The reaction discharge from the first stage has to be neutralized with base and freed from the homogeneous catalyst (triethylaluminium) by distillation. In industrial practice, this is very complex.

U.S. Pat. No. 2,581,228 describes the heterogeneously catalyzed oligomerization of ethene in the presence of an inert solvent. The solvent should be a relatively high-boiling, inert material, preferably a relatively high-boiling alkene or cycloalkene. The catalyst used is a nickel/aluminium system on silica gel. The reaction mixture is a slurry from which the gel-like catalyst can be recovered. Corresponding expenditure on apparatus will be entailed for this.

SUMMARY OF THE INVENTION

It was an object of the present invention to provide a process for the combined preparation of at least butene and octene from ethene.

In the light of the related art, it was another object of the present invention to specify a completely heterogeneously catalyzed process for the combined preparation of at least butene and octene from ethene, which may be operated without a complex catalyst removal and yet does not contaminate downstream, homogeneously catalyzed processes. The resulting products should be as linear as possible. In addition, the process should be able to be carried out as far as possible in the liquid phase in order to be compatible with established technologies for utilization of butene and octene. This saves costly new developments within a complex production group. In addition, the process should also be capable of additionally preparing hexene as the third target product in addition to the two target products butene and octene. Namely, the demand for these olefins can fluctuate. The process accordingly should be able to react to changing market requirements. This is a further essential object which underlies the invention.

These and other objects are achieved by a process for the combined preparation of at least butene and octene from ethane, said process comprising:

a) providing an inert solvent having a boiling point or boiling range below the boiling point of butene;

b) providing a first feed mixture comprising at least the inert solvent and ethene dissolved therein;

c) converting the first feed mixture in a first synthesis;

d) in the first synthesis, oligomerizing at least a portion of the ethene present in the first feed mixture in the presence of a first heterogeneous catalyst and in the presence of the inert solvent to obtain a first reaction mixture comprising at least the inert solvent, butene, hexene and octene;

e) working-up of the first reaction mixture and/or a substance stream based thereon into a low boiler fraction comprising the inert solvent, at least one $C_4$-fraction comprising butenes, a $C_6$-fraction comprising hexenes, a $C_8$-fraction comprising octenes and into a $C_{8+}$-fraction comprising hydrocarbons having more than eight carbon atoms;

f) using at least a portion of the low boiler fraction for providing the first feed mixture;

g) providing a second feed mixture comprising at least hexene and ethene dissolved in the hexene using at least a portion of the $C_6$-fraction;

h) converting the second feed mixture in a second synthesis, wherein the second synthesis is spatially separated from the first synthesis;

i) in the second synthesis, reacting at least a portion of the ethene present in the second feed mixture with at least a portion of the hexene present in the second feed mixture in the presence of a second heterogeneous catalyst to obtain a second reaction mixture comprising at least octene; and k) joint working-up of the second reaction mixture with the first reaction mixture or with the substance stream based thereon.

Figure 1:
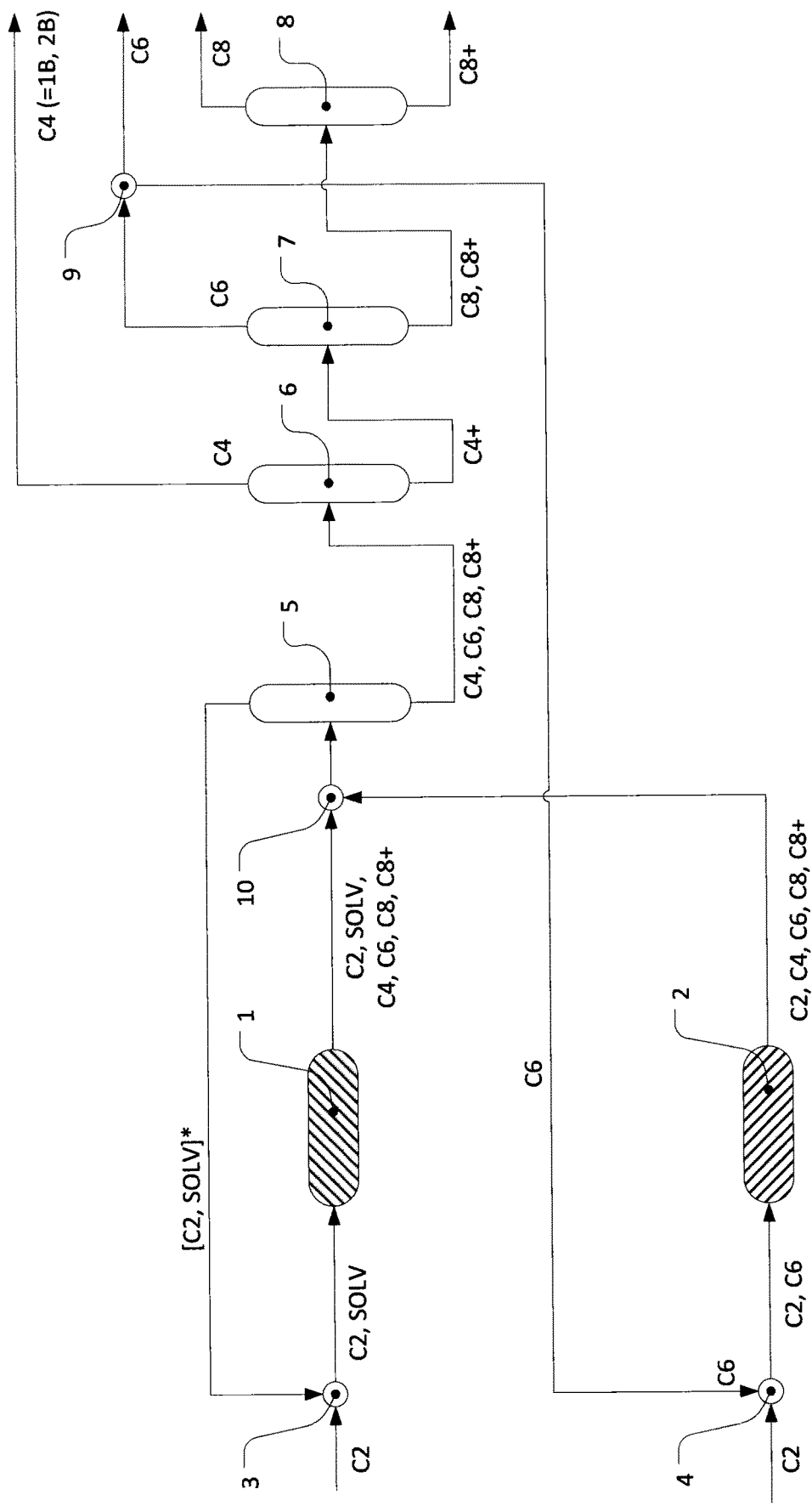
FIG. 1 shows a flow diagram for the basic process.

LIST OF REFERENCE SYMBOLS 1 first synthesis
2 second synthesis
3 mixer for the first synthesis
4 mixer for the second synthesis
5 first distillation column
6 second distillation column
7 third distillation column
8 fourth distillation column
9 divider
10 third mixer
11 fifth distillation column
12 isomerization
13 oxidative dehydrogenation
14 third synthesis
15 fourth mixer
C2 ethene
C4 butene
C6 hexene
C8 octene
C8+ higher oligomers
C12, C12+ olefins having twelve and more carbon atoms
SOLV inert solvent
C2, SOLV first feed mixture
C2, SOLV, C4, C6, C8, C8+ first reaction mixture
[C2, SOLV]* low boiler fraction
C2, C6 second feed mixture
C2, C4, C6, C8, C8+ second reaction mixture
1B 1-butene
2B 2-butene
BD butadiene
C4, C8, C12, C12+ third reaction mixture

DETAILED DESCRIPTION OF THE INVENTION

The basic concept of the present process consists of preparing butene, hexene and octene simultaneously by oligomerizing ethylene in an inert solvent over a heterogeneous catalyst. The use of the heterogeneous catalyst firstly has the advantage that separation from the reaction mixture is simpler than in a homogeneously catalyzed process. In the simplest case, a solid is used as heterogeneous catalyst which remains in the reactor while the fluid reaction mixture is drawn off from the reactor. A special catalyst separation is then practically dispensed with.

An essential aspect of the invention consists of carrying out the reaction in the presence of an inert solvent. More precisely, the ethylene is dissolved in the solvent, the reaction takes place in the solvent and the resulting reaction mixture is discharged from the reactor with the aid of the solvent. The solvent therefore serves as transport medium for the reactants into the reactor and again for the products out from the reactor. This facilitates the handling of the reactants and products on an industrial scale and enables just the simple catalyst removal which, in the simplest case, is separation of a liquid (reaction mixture) from a solid (catalyst). A further advantage of performing the oligomerization in an inert solvent is that the heat of reaction produced during the oligomerization can be transported away from the reactor. For this reason, the reaction can be better controlled and also the product formation influenced since the various oligomers are formed at different rates and at different temperatures. Therefore, not only the residence time but also the temperature of the first synthesis is controlled via the solvent.

The choice of the correct solvent is not arbitrary; on the contrary, it must meet two important preconditions: firstly, in the first synthesis, i.e. the ethene oligomerization, it must act in an inert manner. This means that it must not be consumed in the first reaction and is therefore still available as transport medium for the products and the heat of reaction. The second essential property of the inert solvent consists of its boiling point position in relation to the butenes formed in the first synthesis: The solvent used according to the invention must necessarily have a boiling point which is below the boiling point of the butenes, it only then being possible to distill off the solvent from the reaction mixture at the top together with the unconsumed ethene and to reuse (to recycle) them for provision of the first feed mixture. The greater the gap between the boiling points of the solvent and the butenes, the easier and with more energy-saving the solvent can be separated off, since it has to be evaporated for the separation. The precise boiling point position of the solvent depends on which butenes are formed in the first synthesis. The boiling point of the solvent should be below the boiling point of the butene in the system having the lowest boiling point. A boiling point below that of isobutene (−6.9° C.) should suffice, but in the case that isobutene is not formed in the oligomerization, a boiling point below that of 1-butene (−6.3° C.) is sufficient. In the oligomerization of ethene, no isobutene is generally formed so that a boiling point below −6.3° C. suffices. The boiling points are compared at the same pressure ratios. The temperature values mentioned above are understood to be at standard pressure (1013 hPa). If the inert solvent does not have a singular boiling point but instead a boiling range—for instance because the solvent is not a pure substance but a mixture whose components have different boiling points—then the upper limit of the boiling range of the solvent must be below the lowest boiling point of the butenes present. The reason why the inert solvent according to the invention must have a lower boiling point position than the butenes lies in the fact that the inert solvent can be separated from the work-up stream early on and fed back and for this reason it does not hydraulically burden work-up stages situated downstream.

The early separability of the solvent is also therefore of importance since a second synthesis is provided in accordance with the invention, in addition to the ethene oligomerization, which is likewise not burdened with inert solvent.

A further essential aspect of the invention namely consists of the fact that the hexenes formed in the first reaction (ethene oligomerization) are reacted with further ethylene in a second reaction to give octenes. The reason for this is that in the first synthesis the $C_4$-, the $C_6$- and the $C_8$-oligomers are formed with decreasing selectivity, i.e. mostly butenes, then hexenes and then the octenes. In order to achieve overall a greater yield of octenes, the hexenes are further reacted with ethene in a second, separate synthesis to octenes. Here, the hexene serves as solvent for the ethene. It definitively is not inert in the second reaction but is reacted in a controlled manner, specifically as completely as possible. Nevertheless, the hexene in the second reaction takes on a function like the inert solvent in the first reaction, namely the transport of ethene in the reactor. The transport of the reaction product and the heat of reaction out again from the second reactor is effected however with the second fluid reaction mixture. The advantage of the simple catalyst removal is again achieved here.

Depending on whether directionally more hexenes or more octenes are to be produced by the process, the hexenes formed in the first synthesis are either passed completely into the second synthesis or only a part of the $C_6$-fraction. The remaining hexenes can then be sold as the third target product in addition to the butene and the octene. However, it is also possible to discharge only butene and octene as target product and to convert forcibly the hexene formed in the first synthesis completely to octene in the second synthesis so that none of the hexene exits the process. The hexene balance over the whole process can therefore optionally be neutral or positive. This is only possible, therefore, because the two reactions are carried out spatially separately from each other and because the conversions and the selectivities in the two separate reactions, due to the use of the inert solvent in the first reaction and the hexene as non-inert solvent in the second reaction, can be adjusted to each other.

A further essential aspect of the invention is that the reaction outputs of both syntheses are processed together. Consequently, only one sequence of distillation columns is provided which is charged with both reaction mixtures and thus the olefins present in the fractions separated by the column sequence can originate from both reactions. The additional expense of the double reaction procedure therefore does not mean additional cost for distillation.

Specifically, the process according to the invention is carried out such that the low boiler fraction is separated at the top from the first reaction mixture or from the substance stream based on the first reaction mixture using a first distillation column to obtain an essentially solvent-free bottom product from which in turn the $C_4$-fraction, the $C_6$-fraction, the $C_8$-fraction and the $C_{8+}$-fraction are separated. The feature "solvent-free" refers to the inert solvent used in the first synthesis (the bottom product of the first distillation according to the invention comprises a solvent, namely hexene, which is used as solvent for the second synthesis; however, this is not inert but reactive). As long as the inert solvent has a significant boiling point gap from the butenes produced, it is reasonable to remove the inert solvent completely such that the bottom product is completely free of inert solvent. If the boiling point of the solvent is very close to that of the butenes, however, the complete removal of the solvent signifies a large (energetic) expenditure. In such constellations it is reasonable to leave low amounts of inert solvent in the bottoms of the first distillation. This would then also be "essentially solvent-free" in the context of the invention. The essentially solvent-free bottom product preferably comprises less than 10% by weight inert solvent, even better less than 1% by weight and optionally less than 0.2% by weight inert solvent.

In some variants of the invention, the low boiler fraction, which is separated after the first synthesis and is fed back prior to it, still comprises ethene which was not converted in the first synthesis and/or the second synthesis, in addition to the inert solvent. This is physically possible when the boiling point position of the solvent is between ethene and butene. Ethene is present in this situation when it was not converted completely in the first synthesis (for example, because the residence time was too short) or it was not converted completely in the second synthesis (ethene excess) and the second reaction output is blended with the first reaction mixture prior to the first distillation column. The situation in which the ethene is not converted completely in the first and/or second synthesis can then occur particularly when the process is driven, for example, after reacting to changed demand. Since the ethylene recycling happens automatically via the low boiler fraction—assuming the correct boiling point position of the inert solvent—no process changes in terms of apparatus need to be undertaken; it is sufficient to reduce the feed of fresh ethene when providing the first feed mixture.

The importance of the boiling point position of the inert solvent has already been introduced several times. Examples of pure substances having all required properties of the inert solvent here are propane and isobutane. The boiling point of these $C_3$ and $C_4$-alkanes is between ethene and butene and is therefore suitable for the overhead removal. Methane and ethane cannot be used, however, since they are gaseous under the reaction conditions. The alkanes are inert in the oligomerization compared to ethene and the other olefins. A mixture of propane and isobutane can also be used instead of the pure substances which then leads to a boiling range instead of a singular boiling point. In all mixture ratios these two alkanes lead to an inert solvent having a suitable boiling point position.

The reaction conditions in the first synthesis should be selected as follows:

Temperature: 20° C. to 150° C.; pressure: $1*10^5$ Pa to $50*10^5$ Pa; weight hourly space velocity: 3 to 50 $h^{-1}$. The molar ratio of ethene to solvent in the first feed mixture should be adjusted to a value between 0.1 and 0.5, where the proportion of ethene in the first feed mixture and the reaction conditions of the first synthesis are selected so that the solvent is present in a liquid phase. By selecting the reaction conditions in the ranges specified, with the proviso that the solvent in the first reaction is liquid, this leads to the simple catalyst removal, to the effective removal of the heat of reaction and overall to a high process intensity.

The reaction conditions and the proportion of ethene in the first feed mixture can be selected in the ranges specified such that the ethene is dissolved completely in the liquid solvent or so that the ethene is dissolved partially in the liquid solvent and is present partially in the gas phase. If the ethene is dissolved completely in the liquid inert solvent, the first synthesis (oligomerization) takes place completely in the liquid phase. This is desirable in the interest of the process intensity.

Alternatively, undissolved ethene gas bubbles can form in the liquid feed and reaction mixture. The first synthesis would then be carried out in the bubbling phase. This would have the advantage that right from the start of the reaction a very high proportion of the ethene is consumed so that excess ethene present undissolved in fine gas bubbles redissolves again in the solvent in the following reactor section and therefore again becomes enriched. In addition, the longer presence of ethene resulting effectively therefrom has a positive influence on the $C_4$-relative to the $C_{4+}$-selectivities and the linearity of the alkenes: since branching comes about by desorption and readsorption on the active catalyst centre and ethene in the readsorption competes successfully for the binding sites, this leads to shorter chains and to a preference for the alternative mechanism (progressive chain-lengthening instead of desorption/adsorption). Overall this means enhanced formation of linear 1- and 2-alkenes in the bubbling phase.

In the interest of process intensity, the reaction conditions in the second synthesis (reacting ethene with hexene to give octene) should be selected such that the proportion of ethene in the second feed mixture is in the range from 0.1% by weight to 30% by weight and that the second synthesis is carried out at a temperature in the range from 20° C. to 150° C. and at a pressure in the range from $1*10^5$ Pa to $50*10^5$ Pa, where the proportion of ethene in the second feed mixture and the reaction conditions of the second synthesis are selected so that the hexene is present in a liquid phase and the ethene is completely dissolved therein. A bubbling phase in the second reaction is undesirable since more $C_4$ would thus be formed. The proportion of ethene in the second feed mixture should be selected as low as possible so that the ethene is as far as possible converted completely. The second feed mixture preferably has less ethene than hexene and the proportion of ethene in the second feed mixture should be less than 30% by weight, even better less than 20% by weight.

Optimally, the process is conducted such that the hexene required in the second synthesis is formed completely in the first synthesis. The first reaction mixture is therefore exclusively provided using at least a portion of the $C_6$-fraction and by adding ethene. This means that no hexene has to be fed extraneously. The hexene balance is then not negative over the whole process. Not negative signifies either neutral or positive.

In the case of a neutral hexene balance, the second reaction mixture is provided exclusively using the whole $C_6$-fraction and by adding ethene. This signifies that the total hexene formed in the first synthesis is consumed again in the second synthesis to give octene. The whole process is balanced, i.e. no hexene is produced so that butene and octane are the only target products which are discharged.

In the case of a positive hexene balance, the second reaction mixture is provided exclusively using a first portion of the $C_6$-fraction and by adding ethene and a second portion of the C6-fraction is discharged. In this case, hexene is a third target product in addition to butene and octene. However, this assumes an overproduction of hexene in the first synthesis relative to the consumption in the second synthesis. The production of octene, therefore, decreases in favour of the production of hexene.

The process can also be operated alternating between a neutral and positive hexene balance if the demand for hexene or octene changes in opposing directions. The apparatus of the plant does not have to be changed, only the reaction conditions should be altered in order that the catalysts used in the first and second synthesis cause different selectivity.

A heterogeneous catalyst for controlling this contains at least two components, where the first component comprises at least one element which is selected from among Ni, Cr, Fe, Ti and is present in metallic and/or oxidic and/or hydridic form and the second component comprises at least one metal oxide selected from among $Al_2O_3$, $SiO_2$, $TiO_2$, $ZrO_2$. An example of a catalyst of this kind is known from U.S. Pat. No. 2,581,228.

A particular advantage of a catalyst characterized here is that it can be used both in the first synthesis and in the second synthesis since it catalyzes both reactions. Its selectivity in the respective reaction can be influenced by changing the reaction conditions so that more butene, more hexene or more octene can be produced with it, depending on the demand situation. In the case of oligomerization in inert solvents, however, it always forms more $C_4$-oligomers than $C_6$-oligomers and the more than $C_8$-oligomers and higher oligomers ($C_{8+}$). However, in the case of hexene as solvent, the ratio shifts to more $C_8$ and less $C_6$, so that more octene than hexene is formed. It is surprising that this catalyst also accelerates the conversion of $C_2$ and $C_6$ to $C_8$ and is for this reason also usable in the second synthesis. This is not derivable from U.S. Pat. No. 2,581,228. Therefore, the same catalyst can be used in both reactions. It is also possible, however, to use two different catalysts which are optimized for the particular reaction.

With the aid of the attached Figures, some examples of a process according to the invention will now be illustrated in detail. The drawings show:

FIG. 1: Flow diagram for basic process

Figure 2:
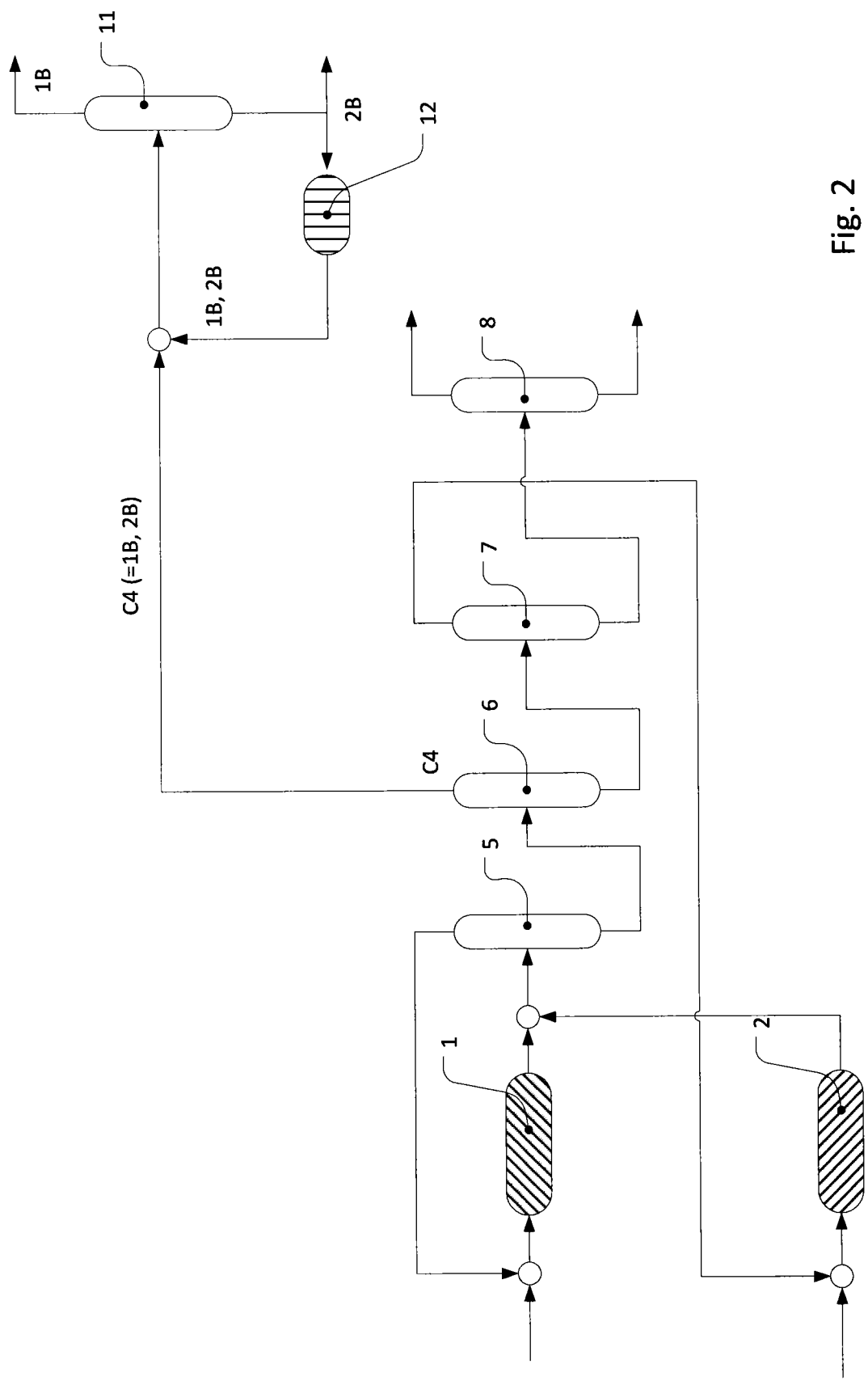
FIG. 2 shows the same as FIG. 1, additionally with isomerization.

FIG. 2: the same as FIG. 1, additionally with isomerization

Figure 3:
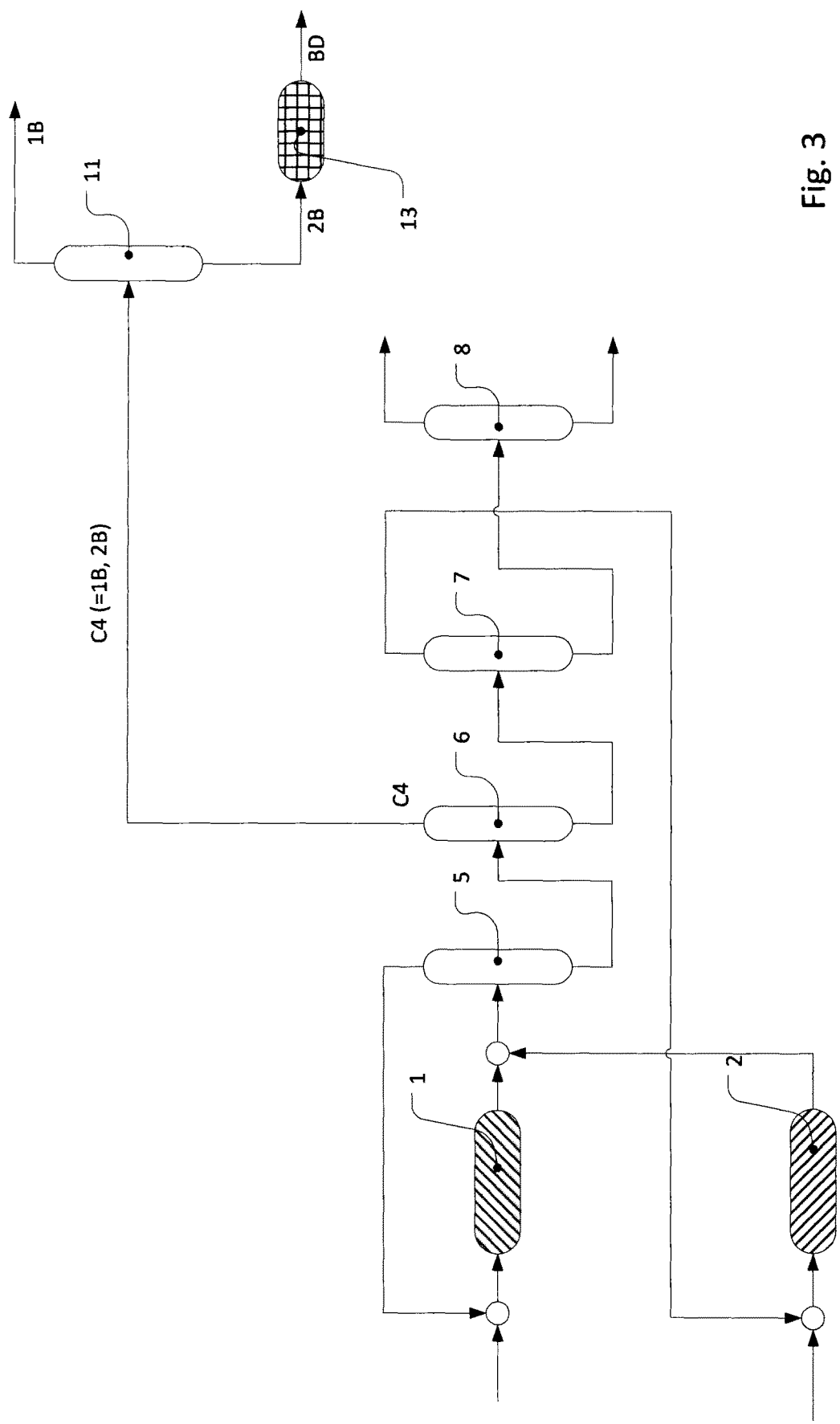
FIG. 3 shows the same as FIG. 1, additionally with oxidative dehydrogenation.

FIG. 3: the same as FIG. 1, additionally with oxidative dehydrogenation

Figure 4:
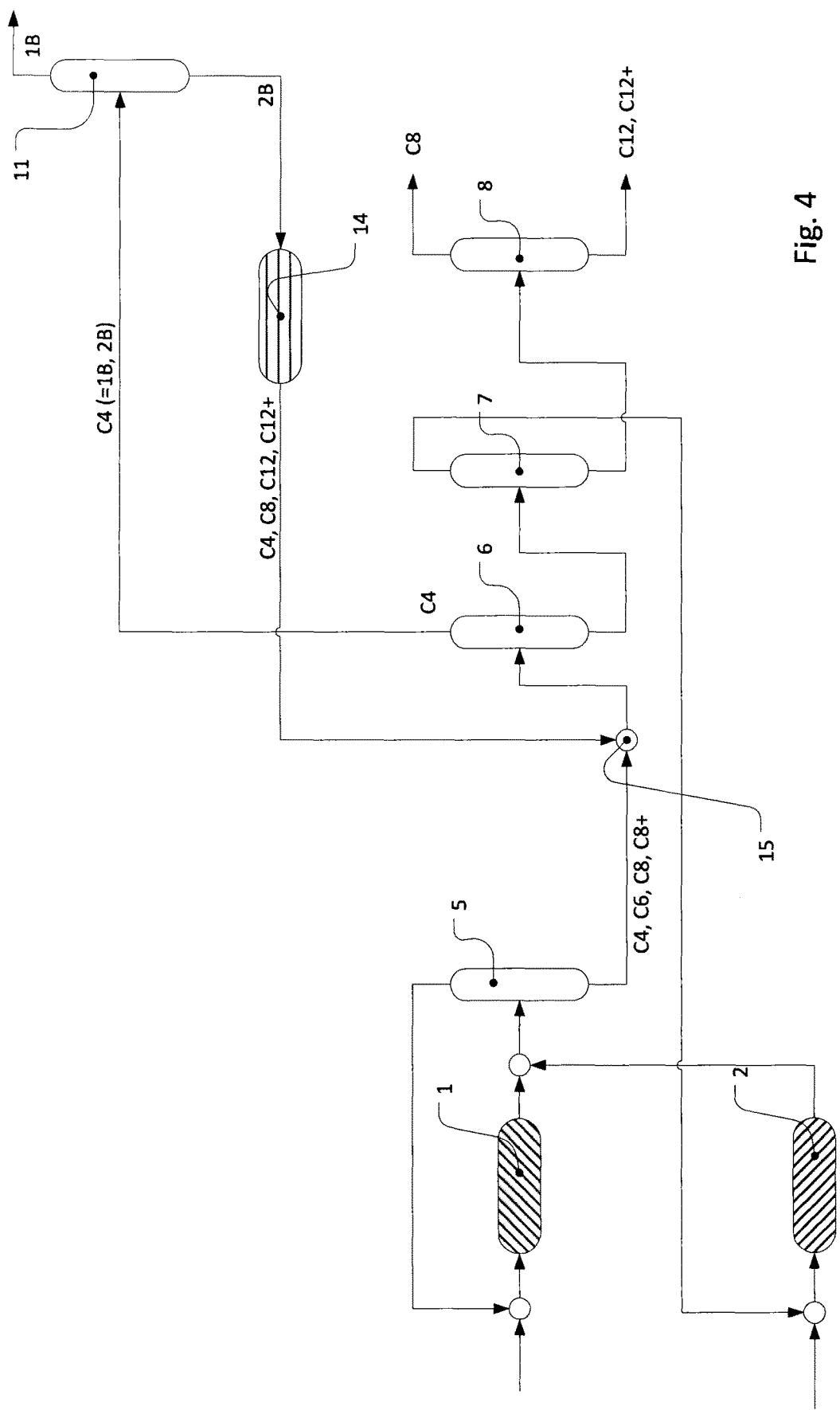
FIG. 4 shows the same as FIG. 1, additionally with a downstream OCTOL process.

FIG. 4: the same as FIG. 1, additionally with downstream OCTOL® process

All figures are schematic and merely show the essential constituents of a corresponding plant for carrying out the process of the invention.

FIG. 1 shows the basic principle. There are two syntheses 1, 2 which are operated in parallel and are carried out in physically separate reactors. The first synthesis 1 is an oligomerization of ethene. It serves primarily for preparing butene but also produces in addition hexene and octene. The second synthesis 2 serves for preparing octene from ethene and hexene.

The ethene C2 required for the two syntheses 1, 2 originates from one or more sources which are not shown here. The purity of the ethene C2 which flows in as a liquid or gas is more than 99.9%. As accompanying materials, it is possible for less than 10 ppm of oxygen, less than 5 ppm of carbon monoxide, less than 10 ppm of carbon dioxide and less than 1000 ppm of other hydrocarbons to occur. A higher purity is not necessary since the most frequent impurities are inert alkanes such as ethane or methane which do not interfere in the reaction itself and, in the case of relatively high proportions, merely change the boiling and pressure ranges slightly.

A mixer 3, 4 is assigned to each synthesis 1, 2. The first mixer 3 serves to provide a first feed mixture C2, SOLV for the first synthesis 1. The first feed mixture is a liquid mixture of an inert solvent SOLV and ethene C2 completely dissolved therein. Propane or isobutane or a mixture thereof can be used as inert solvent SOLV. As the solvent SOLV acts in an inert manner, it is not consumed in the process. It can therefore be recycled. Therefore, the solvent SOLV, which is required in the first mixer 3 for providing the first feed mixture C2, SOLV, originates from a recycled low boiler fraction [C2, SOLV]* whose origin will be elucidated further.

The composition of the first feed mixture is set in the first mixer 3 so that it is liquid under the reaction conditions in the first synthesis and the ethene is completely dissolved in the solvent.

In the first synthesis 1, the ethene is oligomerized in the presence of a first heterogeneous catalyst and in the presence of inert solvent SOLV. Here, butenes C4 are formed as dimers, hexenes C6 as trimers, octenes C8 as tetramers of the ethene and also higher olefins C8+. The selectivity of the first synthesis decreases with the chain length of the oligomers, i.e. primarily butenes are formed, then hexene and even less octene and hardly any higher C8+ olefins. Part of the ethene C2 is not reacted. Overall, the first reaction output comprises C2, SOLV, C4, C6, C8, C8+, i.e. unreacted ethene and its oligomers butene, hexene, octene and higher olefins. Since the solvent SOLV acts in an inert manner in the reaction, it is found again in the first reaction mixture.

The first reaction mixture C2, SOLV, C4, C6, C8, C8+, SOLV is worked up by distillation with the aid of a series of four columns 5, 6, 7, 8. The first distillation column 5 separates off at the top the low boiler fraction [C2, SOLV]* already mentioned. The low boiler fraction contains unreacted ethene C2 and the solvent SOLV. Since the solvent owing to its boiling point position boils below the butene C4, the oligomers C4, C6, C8 and C8+ remain in the bottoms of the first distillation column 5. The bottoms of the first distillation column 5 is free from the inert solvent SOLV. The subsequent process steps are therefore not burdened with the solvent. Instead, the solvent is recovered completely from the first distillation column and is recycled to the first mixer 3. There, it is reused in providing the first feed mixture C2, SOLV. For the desired high conversion in the first synthesis, however, the low boiler fraction should contain hardly any ethene.

The second distillation column 6 then separates off the butenes C4 originating from the first reaction mixture as a $C_4$-fraction at the top. The $C_4$-fraction contains essentially 1-butene 1B and cis/trans-2-butene 2B. The butenes are the first target product of the process. If 1-butene is of particular interest, the C4-fraction can be processed still further. This is described by means of FIGS. 2 to 4.

The olefins having more than four carbon atoms C4+ are conveyed from the bottom of the second distillation column 6 into the third distillation column 7. There, a C6-fraction is separated off at the top comprising the hexenes C6. Octene C8 and the higher olefins C8+ remain in the bottoms of the third distillation column 7.

Depending on the demand for hexene as a separate target product, the C6-fraction at the top of the third distillation column is divided in a divider 9 into a portion which is discharged from the process and a portion which is conveyed to the second mixer 4. In the case that hexene is not in demand separately as third target product, the complete C6-fraction is conveyed to the second mixer 4. Such a scenario is shown in FIGS. 2, 3 and 4. It is not possible, however, to withdraw the complete C6-fraction from the process since the hexene contained therein is required as solvent in the second synthesis. In the divider 9, no separation of the fraction takes place, both portions thus having the same composition and consisting essentially of hexene C6.

In the second mixer 4, fresh ethene C2 is dissolved in the hexene C6 from the C6-fraction, such that a second feed mixture C2, C6 is formed. The composition of the second feed mixture C2, C6 is set in the second mixer 4 so that it is liquid under the reaction conditions in the second synthesis 2 and the ethene is completely dissolved in the hexene.

In the second synthesis 2, ethene C2 and hexene C6 are then reacted in the presence of a heterogeneous catalyst to form octene C8. In addition, secondary reactions still take place in the second synthesis 2 since butenes C4 and higher olefins C8+ are also formed there. In addition, it is possible to conceive that octene is formed by tetramerization of ethene in the second synthesis.

If there is no interest in hexene as a separate commercial product, the second synthesis 2 is operated so that the amount of hexene formed in the first synthesis 1 is consumed again in the second synthesis 2. A buildup of hexene in the plant is thus avoided. In the case that hexene is in demand externally and is for this reason discharged proceeding from divider 9, less hexene is available for the second synthesis 2 such that also less octene can be formed. In this respect, a competition exists between C6 and C8 yield of the overall process. The feature of the process according to the invention, however, is that it can be operated variably between a neutral and positive hexene balance and accordingly can additionally offer also hexene as target product in addition to butene and octene.

The second reaction mixture C2, C4, C6, C8, C8+, taken off from the second synthesis comprises the same olefins as the first reaction mixture but in a different composition. The inert solvent SOLV is not present in the second reaction mixture. The second synthesis 2 forms predominantly octene (besides butene), so that the C8 content of the second reaction mixture is higher than that in the first reaction mixture. The latter in turn has a distinctly higher C4 content.

Owing to the similar composition, the second reaction mixture can be worked up together with the first reaction mixture. For this purpose, the first reaction mixture is mixed with the second reaction mixture in a third mixer 10 so that a substance stream based on the first reaction mixture is formed which is fed into the column series 5, 6, 7, 8.

Octene C8 is taken off as second target product from the top of the fourth and last distillation column 8 of the column series 5, 6, 7, 8, while the higher olefins C8+ remain in the bottoms and are separately utilized as unavoidable by-product.

Once again back to the first target product butene C4 which is obtained as $C_4$-fraction at the top of the second column 6.

The butene C4 obtained there is not isomerically pure, but instead is an isomer mixture 1B, 2B composed of 1-butene and cis-2-butene and trans-2-butene. The overhead product from the second distillation column 6 is thus linear n-butene. Gratifyingly, no branched isobutene is present, since this is not formed in the first synthesis. A complicated removal of isobutene, which is necessary in the isolation of n-butene from C4 streams, can therefore be dispensed with in this process based on ethene.

The economics of the process can be improved by the butene mixture C4 from the top of the second column 6 being worked up further in the direction of 1-butene. FIGS. 2, 3 and 4 each show a proposal for this.

A feature common to these three variants is a fifth distillation column 11 which is provided for separation of 1-butene 1B and 2-butene 2B by distillation. 1-Butene 1B has a lower boiling point than cis-2-butene and trans-2-butene and can therefore be taken off in high purity from the top of the fifth distillation column 1. There are then three possibilities for use of the 2-butene 2B at the bottom of the fifth distillation column 11:

In the first variant as shown in FIG. 2, the 2-butene is subjected to an isomerization 12 which partly converts the 2-butene into 1-butene. The isomerization 12 again results in an isomer mixture 1B, 2B of 1-butene and 2-butene which is mixed with the C4-fraction and is again fed into the fifth distillation column 11. For thermodynamic reasons, the isomerization of the 2-butene can never be complete. It is therefore necessary for 2-butene 2B to be continually discharged from the bottom of the fifth distillation column 11.

As an alternative, the 2-butene 2B from the bottom of the fifth distillation column 11 can be subjected to an oxidative dehydrogenation 13. This is shown in FIG. 3. In the oxidative dehydrogenation 13, the 2-butene is converted into 1,3-butadiene BD, which is a chemical having greater added value than 2-butene, so that the process facilitates a fourth target product. The oxidative dehydrogenation can also be preceded by an isomerization of 2-butene to 1-butene since 1-butene reacts more rapidly to form butadiene than does 2-butene. The optional isomerization is not shown in FIG. 3.

Finally, as shown in FIG. 4, the 2-butene 2B from the bottom of the fifth distillation column 11 can be fed to a third synthesis 14 in which it is at least partly oligomerized to octene. This preferably occurs in an OCTOL® process which forms not only dibutene but also olefins having twelve and more carbon atoms C12, C12+. The third reaction mixture C4, C8, C12, C12+ obtained in this way is mixed with the solvent-free bottoms C4, C6, C8 and C8+ from the first distillation column 5 in a fourth mixer 15 and fed to the second distillation column 6. The work-up of the third reaction mixture thus occurs together with the first reaction mixture and the second reaction mixture. The higher olefins C12, C12+ formed in the third synthesis 14 end up in the bottoms of the fourth distillation column 8 and are discharged there or are further processed from there.

Having generally described this invention, a further understanding can be obtained by reference to certain specific examples which are provided herein for purposes of illustration only, and are not intended to be limiting unless otherwise specified.

EXAMPLES

Example 1

Oligomerization of Ethene in Isobutane 15.5 g of a heterogeneous catalyst based on nickel and silica-alumina (cf. U.S. Pat. No. 2,581,228) were introduced into a tube reactor which had a length of 1 m and an internal diameter of 6 mm and whose temperature was controlled from the outside by means of oil. A mixture of 14.5% by mass of ethene and 85.5% by mass of isobutane was subsequently passed through at a total flow rate of 98 g/h and a temperature of 70° C. (WHSV=6.3). The pressure was kept constant at 30 bar. After a time of approximately 60 hours, a state in which the conversion no longer changed had been reached. The results are summarized in Table 1. For further analysis, the product fraction was injected into a hydrogenating gas chromatograph. The compositions of the hydrogenated C8 fraction are likewise summarized in Table 1.

Example 2

Oligomerization of Ethene in and with n-Hexene

In a manner analogous to Example 1, 15.5 g of the same catalyst were introduced into a tube reactor which had a length of 1 m and an internal diameter of 6 mm and whose temperature was controlled from the outside by means of oil. A mixture of 20% by mass of ethene, 73% by mass of n-hexene and 7% by mass of the internal standard n-heptane was subsequently passed through at a total flow rate of 105 g/h and a temperature of 70° C. (WHSV=6.8/h). The pressure was kept constant at 30 bar. After a time of 73 hours, a state in which the conversion no longer changed had been reached. The results and the composition of the hydrogenated C8 fraction are summarized in Table 1.

TABLE 1

| | | | | | | 1- | 2- | Sel. | Sel. | Sel. |
| Example | Conversion | C4 | C6 | C8 | C8+ | butene | butene | nO | MH | DMH |
| --- | --- | --- | --- | --- | --- | --- | --- | --- | --- | --- |
| 1 | 97% | 67% | 28% | 5% | 1% | 28% | 72% | 47% | 47% | 5%[a] |
| 2 | 98% | 58% | 8%[c] | 25% | 9% | 45% | 55% | 30% | 68% | 2%[b] |

Experimental results

The iso index of the C8 mixture is for a) 0.57 and for b) 0.72.
c) C6 results from freshly formed hexene minus the hexene consumed.

The abbreviations have the following meanings: Sel. is selectivity, nO is n-octene, MH is methylheptene and DMH is dimethylhexene.

CONCLUSION

Example 1 shows that the use of an inert solvent in ethene oligomerization leads to the formation of comparatively more butene and distinctly more hexene than in Example 2 and in contrast hardly any octene. (This effect and the 1-butene selectivity could be enhanced by even higher C2 concentrations.) At the same time, an octene having a significantly lower iso index is formed in the inert solvent than in the reaction of ethene with hexene, which results particularly from the reaction of the thermodynamically more stable 2- and 3-hexene dominating in the C6 mixture and therefore the enhanced formation of a mono-branched octene in Example 2. As desired, the C8 proportion can obviously be increased at the cost of the C6 proportion by using hexene as solvent in the second synthesis.

European patent application No. EP15151624.2 filed Jan. 19, 2015, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for the combined preparation of at least butene and octene from ethene, the process comprising:
   a) providing an inert solvent;
   b) mixing ethene having a purity of more than 99.9% and said inert solvent to provide a first feed mixture comprising said inert solvent and ethene dissolved therein;
   c) in a first synthesis, oligomerizing at least a portion of the ethene present in the first feed mixture in the presence of a first heterogeneous catalyst to obtain a first reaction mixture comprising said inert solvent, butenes, hexenes and octenes;
   d) working-up of the first reaction mixture and/or a stream based thereon into a low boiler fraction comprising the inert solvent, at least one $C_4$-fraction comprising butenes, a $C_6$-fraction comprising hexenes, a $C_8$-fraction comprising octenes and into a $C_{8+}$-fraction comprising hydrocarbons having more than eight carbon atoms;
   e) recycling at least a portion of the low boiler fraction to the first feed mixture;
   f) mixing hexene and ethene to provide a second feed mixture comprising ethene dissolved in the hexene wherein hexene is provided using at least a portion of the $C_6$-fraction;
   g) in a second synthesis, reacting at least a portion of the ethene present in the second feed mixture with at least a portion of the hexene present in the second feed mixture in the presence of a second heterogeneous catalyst to obtain a second reaction mixture comprising at least octene, wherein the second synthesis is spatially separated from the first synthesis; and
   h) feeding the second reaction mixture to the working-up of said first reaction mixture;
   wherein said inert solvent has a boiling point or boiling range below any butene formed in said first synthesis;
   a solid is used as the first heterogenous catalyst and/or the second heterogenous catalyst which comprises at least two components,
   wherein a first component comprises at least one element selected from the group consisting of Ni, Cr, Fe, and Ti, which is present in a metallic and/or oxidic and/or hydridic form, and
   wherein a second component comprises at least one metal oxide selected from the group consisting of $Al_2O_3$, $SiO_2$, $TiO_2$, and $ZrO_2$ and mixtures thereof.

2. The process according to claim 1, wherein the low boiler fraction is separated at the top from the first reaction mixture or from the substance stream based on the first reaction mixture using a first distillation column to obtain an essentially solvent-free bottom product from which in turn the $C_4$-fraction, the $C_6$-fraction, the $C_8$-fraction and the $C_{8+}$-fraction are separated.

3. The process according to claim 2, wherein the low boiler fraction in the first synthesis and/or in the second synthesis comprises unreacted ethene in addition to said inert solvent.

4. The process according to claim 1, wherein said inert solvent is propane or isobutane or a mixture thereof.

5. The process according to claim 1 said first synthesis is carried out at the following conditions with the provision that said inert solvent is present in a liquid phase in said oligomerizing:
   Temperature: 20° C. to 150° C.,
   Pressure: $1*10^5$ Pa to $50*10^5$ Pa,
   Weight hourly space velocity: 3 to 50 $h^{-1}$, and
   a molar ratio of ethene to said solvent in the first feed mixture is adjusted to a value of 0.1 to 0.5.

6. The process according to claim 5, wherein the ethene is completely dissolved in the liquid inert solvent at the first synthesis conditions.

7. The process according to claim 5, wherein the ethene is partially dissolved in the liquid inert solvent and is present partially in the gas phase at the first synthesis conditions.

8. The process according to claim 1, wherein the second feed mixture comprises ethene at a proportion of from 0.1% by weight to 30% by weight and wherein the second synthesis is carried out at a temperature of from 20° C. to 150° C. and at a pressure of from $1*10^5$ Pa to $50*10^5$ Pa, wherein the proportion of ethene in the second feed mixture and the reaction conditions of the second synthesis are selected so that the hexene is present in a liquid phase and the ethene is completely dissolved therein.

9. The process according to claim 1, wherein the second reaction mixture is provided exclusively using at least a portion of the $C_6$-fraction and by adding ethene.

10. The process according to claim 9, wherein the second reaction mixture is provided exclusively using a first portion of the $C_6$-fraction and by adding ethene and that a second portion of the $C_6$-fraction is discharged.

11. The process according to claim 9, wherein the second reaction mixture is provided exclusively using the entire $C_6$-fraction and by adding ethene.

12. The process of claim 1, wherein said first reaction mixture further comprises ethene and said low boiler fraction comprises ethene and said inert solvent.

13. The process of claim 1, further comprising discharging the first reaction mixture from a reactor with said inert solvent as a transport medium after the first synthesis.

14. A process for the combined preparation of at least butene and octene from ethene, the process comprising:
  a) providing an inert solvent;
  b) mixing ethene having a purity of more than 99.9% and said inert solvent to provide a first feed mixture comprising said inert solvent and ethene dissolved therein;
  c) in a first synthesis, oligomerizing at least a portion of the ethene present in the first feed mixture in the presence of a first heterogeneous catalyst to obtain a first reaction mixture comprising said inert solvent, butenes, hexenes and octenes;
  d) working-up of the first reaction mixture and/or a stream based thereon into a low boiler fraction comprising the inert solvent, at least one $C_4$-fraction comprising butenes, a $C_6$-fraction comprising hexenes, a $C_8$-fraction comprising octenes and into a $C_{8+}$-fraction comprising hydrocarbons having more than eight carbon atoms;
  e) recycling at least a portion of the low boiler fraction to the first feed mixture;
  f) mixing hexene and ethene to provide a second feed mixture comprising ethene dissolved in the hexene wherein hexene is provided using at least a portion of the $C_6$-fraction;
  g) in a second synthesis, reacting at least a portion of the ethene present in the second feed mixture with at least a portion of the hexene present in the second feed mixture in the presence of a second heterogeneous catalyst to obtain a second reaction mixture comprising at least octene, wherein the second synthesis is spatially separated from the first synthesis; and
  h) feeding the second reaction mixture to the working-up of said first reaction mixture;
  wherein said inert solvent has a boiling point or boiling range below any butene formed in said first synthesis;
  a solid is used as the first heterogenous catalyst which comprises at least two components,
  wherein a first component comprises at least one element selected from the group consisting of Ni, Cr, Fe, and Ti, which is present in a metallic and/or oxidic and/or hydridic form, and
  wherein a second component comprises at least one metal oxide selected from the group consisting of $Al_2O_3$, $SiO_2$, $TiO_2$, and $ZrO_2$ and mixtures thereof.

15. The process of claim 14, wherein a solid is used as the second heterogenous catalyst which comprises at least two components,
  wherein a first component of said second heterogeneous catalyst comprises at least one element selected from the group consisting of Ni, Cr, Fe, and Ti, which is present in a metallic and/or oxidic and/or hydridic form, and
  wherein a second component of said second heterogeneous catalyst comprises at least one metal oxide selected from the group consisting of $Al_2O_3$, $SiO_2$, $TiO_2$, and $ZrO_2$ and mixtures thereof.

16. The process of claim 14, further comprising discharging the first reaction mixture from a reactor with said inert solvent as a transport medium after the first synthesis.

17. The process of claim 14, wherein said first reaction mixture further comprises ethene and said low boiler fraction comprises ethene and said inert solvent.

* * * * *